(12) United States Patent
Halden

(10) Patent No.: US 9,341,609 B2
(45) Date of Patent: May 17, 2016

(54) METHODS AND SYSTEMS FOR ULTRA-TRACE ANALYSIS OF LIQUIDS

(75) Inventor: Rolf U. Halden, Phoenix, AZ (US)

(73) Assignee: ARIZONA BOARD OF REGENTS ACTING FOR AND ON BEHALF OF ARIZONA STATE UNIVERSITY, Scottsdale, AZ (US)

( * ) Notice: Subject to any disclaimer, the term of this patent is extended or adjusted under 35 U.S.C. 154(b) by 755 days.

(21) Appl. No.: 13/695,395

(22) PCT Filed: May 4, 2011

(86) PCT No.: PCT/US2011/035255
§ 371 (c)(1),
(2), (4) Date: Oct. 30, 2012

(87) PCT Pub. No.: WO2011/140270
PCT Pub. Date: Nov. 10, 2011

(65) Prior Publication Data
US 2013/0040290 A1    Feb. 14, 2013

Related U.S. Application Data

(60) Provisional application No. 61/331,482, filed on May 5, 2010.

(51) Int. Cl.
*G01N 1/10*     (2006.01)
*C12M 1/34*     (2006.01)
(Continued)

(52) U.S. Cl.
CPC .......... *G01N 33/1826* (2013.01); *E21B 49/082* (2013.01); *G01N 1/405* (2013.01); *G01N 33/24* (2013.01)

(58) Field of Classification Search
CPC ....... E21B 49/082; E21B 49/08; G01N 33/24; G01N 33/1826; G01N 33/184; G01N 33/1866; G01N 2001/1031; G01N 1/14; G01N 2001/1427; G01N 1/405; G01N 1/4005; Y10T 436/25375; C12Q 1/24; E02D 1/06; B01D 15/002; B01D 15/005; B01D 15/004; B01D 27/142; B01D 27/144; B01D 29/005; B01D 29/0056; B01D 29/52; B01D 29/54
See application file for complete search history.

(56) References Cited

U.S. PATENT DOCUMENTS 2,609,878 A    9/1952  Halliburton
4,628,748 A    12/1986 Jogan et al.
(Continued)

FOREIGN PATENT DOCUMENTS

WO    WO0114852 A1    3/2001
WO    2004081530 A2   9/2004
(Continued)

OTHER PUBLICATIONS

Canosa, P. et al. "Optimization of solid-phase microextraction conditions for the determination of triclosan and possible related compounds in water samples." J. Chromatography A (2005) 1072 107-115.*

(Continued)

*Primary Examiner* — Christopher A Hixson
(74) *Attorney, Agent, or Firm* — George A. Leone; Citadel Patent Law

(57) ABSTRACT

A monitoring assembly (201) with an intake (213) has at least one pump (210) featuring at least one pump channel mounted in the monitoring assembly (201). A plurality of fluid lines are coupled to the at least one pump (210). At least one filter cartridge (315) is also mounted in the assembly. Each filter cartridge (315) is separately coupled by one of the plurality of fluid lines to one of the pump channels, where each filter cartridge (315) contains material for extracting an analyte, and where the at least one pump operates to separately push fluid through the at least one filter cartridge (315). The filter cartridge (315) operates to separate fluid into constituent parts.

13 Claims, 15 Drawing Sheets

(51) Int. Cl.

| | |
|---|---|
| C12Q 1/14 | (2006.01) |
| C12Q 1/70 | (2006.01) |
| C12Q 1/04 | (2006.01) |
| G01N 33/18 | (2006.01) |
| E21B 49/08 | (2006.01) |
| G01N 1/40 | (2006.01) |
| G01N 33/24 | (2006.01) |

(56) References Cited

U.S. PATENT DOCUMENTS

| | | | |
|---|---|---|---|
| 4,727,936 A | | 3/1988 | Mioduszewski et al. |
| 4,804,050 A | * | 2/1989 | Kerfoot ........................... 175/20 |
| 5,138,890 A | | 8/1992 | Wood |
| 5,349,874 A | | 9/1994 | Schapira et al. |
| RE34,754 E | | 10/1994 | Dickinson et al. |
| 5,369,011 A | | 11/1994 | Ebersol et al. |
| 5,559,295 A | | 9/1996 | Sheryll |
| 5,663,492 A | | 9/1997 | Alapati et al. |
| 5,686,299 A | | 11/1997 | Colwell et al. |
| 5,844,147 A | | 12/1998 | Fiedler et al. |
| 6,004,766 A | | 12/1999 | Atrache et al. |
| 6,174,673 B1 | | 1/2001 | Short et al. |
| 6,306,350 B1 | * | 10/2001 | Mereish ................... G01N 1/14 210/445 |
| 6,379,560 B1 | * | 4/2002 | Tilp et al. ................... 210/748.1 |
| 6,561,046 B1 | | 5/2003 | Taylor et al. |
| 7,662,618 B2 | | 2/2010 | Halden |
| 2003/0092056 A1 | * | 5/2003 | Nagasawa ............ G01N 30/466 435/6.14 |
| 2003/0153021 A1 | * | 8/2003 | Lu et al. ........................ 435/7.32 |
| 2004/0180334 A1 | | 9/2004 | Halden |
| 2005/0074834 A1 | | 4/2005 | Chaplen et al. |
| 2007/0161076 A1 | | 7/2007 | Halden |
| 2009/0261261 A1 | * | 10/2009 | Rodgers ................. G01T 1/2008 250/370.11 |
| 2010/0159502 A1 | | 6/2010 | Halden |
| 2011/0003400 A1 | | 1/2011 | Halden |

FOREIGN PATENT DOCUMENTS

| | | |
|---|---|---|
| WO | 2005076887 A2 | 8/2005 |
| WO | 2008057398 A2 | 5/2008 |
| WO | 2009105241 A1 | 8/2009 |

OTHER PUBLICATIONS

Alissa Coes, et al; "Sampling trace organic compounds in water: a comparison of a continuous active sampler to continuous passive and discrete sampling methods", Science of the Total Environment vol. 473-474, p. 731-741.
"Continuous Low-Level Aquatic Monitoring", The C.L.A.M., C.I. Agent Storm-water Solutions, Aqualytical poster.
Jamie Aderhold, "New Ultra-Low Detection Technique for Hydrophobic Organic Contaminants", C.I.Agent Storm-Water Solutions, Aqualytical.
"Versatile and Proven Water Monitoring Solutions", C.I.Agent Continuous Low-level Aquatic Monitoring Cover Sheet.
"Water Monitoring Products" C.I.Agent Storm-Water Solutions, (2013), <http://www.ciagent-stormwater.com/new-water-monitoring/>.
Michael Ensminger, Study 289: Method Development for the Continuous Low-Level Aquatic Monitoring (C.L.A.M.) Sampler for Monitoring Urban Surface Water (FY2013-2014), (2013), Department of Pesticide Regulation Environmental Monitoring Branch Sacramento California, p. 1-11.
Alan Kolok, "Passive Integrative Water Samplers for Pesticides: Methodology, Quantification and Water Quality Assessment.", Aquatic Toxicology Laboratory of University of Nebraska Omaha.
Brent Hepner, "Time Integrative in Situ Field Extraction Techniques and Advantages", C.I.Agent Storm-Water Solutions, Aqualytical Poster.

Chalew, Talia E., et al., "Environmental Exposure of Aquatic and Terrestrial Biota to Triclosan and Triclocarban," J. Am. Water Works Assoc., 2009, pp. 4-13, vol. 45, No. 1.
Colqhoun, David R., et al., "Global Screening of Human Cord Blood Proteomes for Biomarkers of Toxic Exposure," Environ. Health Persp., May 2009, pp. 832-838, vol. 117, No. 5.
Deo, Randhir P., et al., "Empirical Model for Predicting Concentrations of Refractory Hydrophobic Organic Compounds in Digested Sludge," Environ Chem., Dec. 2009, pp. 544, vol. 6, No. 6.
Deo, Randhir P., et al., "Effect of Sample Filtration on the Quality of Monitoring Data Reported for Organic Compounds during Wastewater Treatment," J. Environ. Monit., Feb. 2010, pp. 478-483, vol. 12, No. 2.
Dong, Wenming, et al., "Sorption and Bioreduction of Hexavalent Uranium at a Military Facility by the Chesapeake Bay," Jul. 2006, Env. Pollut., pp. 132-142, vol. 142, No. 1.
Halden, Rolf U., et al., "Degradation of 3-phenoxybenzoic Acid in Soil by Pseudomonas pseudoalcaligenes POB310 (pPOB) and Two Modified Pseudomonas Strains," Appl. Environ. Microbiol., Aug. 1999, pp. 3354-3359, vol. 65, No. 8.
Halden, Rolf U., et al., "Removal of Dibenzofuran, Dibenzo-p-Dioxin, and 2-Chlorodibenzo-p-Dioxin from Soils Inoculated with *Sphingomonas* sp. Strain RW1." Appl. Environ. Microbiol., May 1999, pp. 2246-2249, vol. 65, No. 5.
Halden, Rolf U., et al., "Transformation of mono- and dichlorinated phenoxybenzoates by phenoxybenzoate-dioxygenase in Pseudomonas pseudoalcaligenes POB310 and a modified diarylether-metabolizing bacterium," Biotechnol. Bioeng., Jul. 2000, pp. 107-112, vol. 69, No. 1.
Halden, Rolf U., et al., "Evaluation of Standard Methods for the Analysis of MTBE and Related Oxygenates in Gasoline-Contaminated Groundwater," Environ. Sci. Technol., Apr. 2001, pp. 1469-1474, vol. 35, No. 7.
Halden, Rolf U., et al., "Co-Occurrence of Triclocarban and Triclosan in U.S. Water Resources," Environ. Sci. Technol., Mar. 2005, pp. 1420-1426, vol. 39, No. 6.
Halden, Rolf U., "Parallel in Situ Screening of Remediation Strategies for Improved Decision Making, Remedial Design, and Cost Savings," Environmental Security Technology Certification Program (ESTCP), http://www.serdp.org/Program-Areas/Environmental-Restoration/Contaminated-Groundwater/Monitoring/ER-200914.
Heidler, Jochen, et al., "Critical Review: Meta-analysis of Mass Balances for Monitoring Chemical Fate during Wastewater Treatment," Environ. Sci. Technol., Sep. 2008, pp. 6324-6332, vol. 42, No. 17.
Heidler, Jochen, et al., "Fate of Organohalogens in U.S. Wastewater Treatment Plants and Estimated Chemical Releases to Soils Nationwide from Biosolids Recycling," J. Environ. Monit., Dec. 2009, pp. 2207-2215, vol. 11, No. 12.
Higgins, Christopher P., et al., "Bioaccumulation of Triclocarban in Lumbriculus variegates," Environ. Toxicol. Chem., Dec. 2009, pp. 2580-2586, vol. 28, No. 12.
Kim, Sung R., et al., "Volatile Organic Compounds in Human Milk: Methods and Measurements," Environ. Sci. Technol., Mar. 2007, pp. 1662-1667, vol. 41, No. 5.
Koester, Carolyn J., et al., "Analysis of Perchlorate in Groundwater by Electrospray Ionization Mass Spectrometry/Mass Spectrometry," Environ. Sci. Technol., Mar. 2000, pp. 1862-1864, vol. 34, No. 9.
Lowe, Mary, et al, "Geochemistry and microbial diversity of a trichloroethene-contaminated Superfund site undergoing intrinsic in situ reductive dechlorination," FEMS Microbio. Ecol., May 2002, pp. 123-134, vol. 40, No. 2.
Miller, Todd R., et al., "Bacterial Community Analysis of Shallow Groundwater Undergoing Sequential Anaerobic and Aerobic Chloroethene Biotransformation," FEMS Microbiol. Ecol., May 2007, pp. 299-311, vol. 60, No. 2.
Miller, Todd R., et al., Fate of Triclosan and Triclocarban in Estuarine Sediment. Environ. Sci. Technol., 2008, 42:4570-4576 USA.
Rittmann, Bruce E., et al., "Pre-genomic, Genomic and Postgenomic Study of Microbial Communities Involved in Bioenergy," Nature Rev. Microbiol, Aug. 2008, pp. 604-612, vol. 6.

(56) References Cited

OTHER PUBLICATIONS

Sapkota, Amir, et al., "Detection of Triclocarbon and Two Co-Contaminating Chlorocarbanilides in U.S. Aquatic Environments Using Isotope Dilution Liquid Chromatography Tandem Mass Spectrometry," Environ. Res., Jan. 2007, pp. 21-29, vol. 103, No. 1.

Vancheeswaran, Sanjay, et al., "Abiotic and Biological Transformation of Tetraalkoxysilanes and Trichloroethene/cis-1,2-Dichloroethene Cometabolism Driven by Tetrabutoxysilane-Degrading Microorganisms," Environ. Sci. Technol., 1999, pp. 1077-1085, vol. 33, No. 7.

Vancheeswaran, Sanjay, et al., "Intrinsic remediation of trichloroethene driven by tetraalkoxysilanes as co-contaminants: results from microcosm and field studies," Remediation, Spring 2003, pp. 7-25, vol. 13, No. 2.

Young, Thayer A., et al., "Ab Initio and in Situ Comparison of Caffeine, Triclosan, and Triclocarbon as Indicators of Sewage-derived Microbes in Surface Waters," Environ. Sci. Technol., May 2008, pp. 3335-3340, vol. 42, No. 9.

Zhang, Yongyu, et al., "Protein Modifications Relate to Phage Resistance in a Marine Roseobacter," Aquat. Microb. Ecol., 2009, pp. 203-207, vol. 55.

Zhao, Yanlin, et al., "Searching for a 'Hidden' Prophage in a Marine Bacterium," Appl. Environ. Microbiol., Jan. 2010, pp. 589-595, vol. 76, No. 2.

International Search Report and Written Opinion for PCT Application No. PCT/US2011/035255; 9 pages.

International Preliminary Report on Patentability for PCT Application No. PCT/US2011/035255; 5 pages.

* cited by examiner

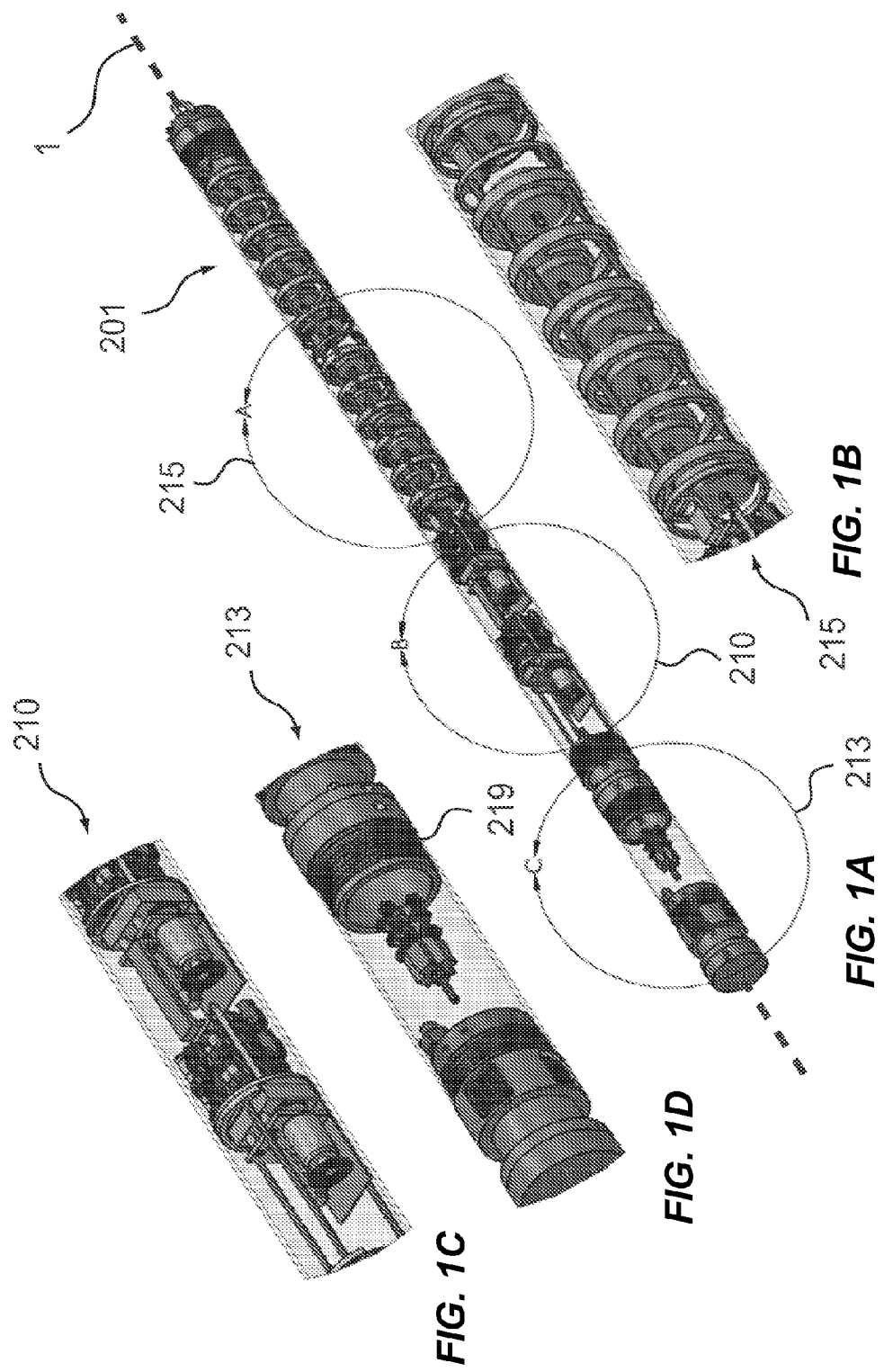

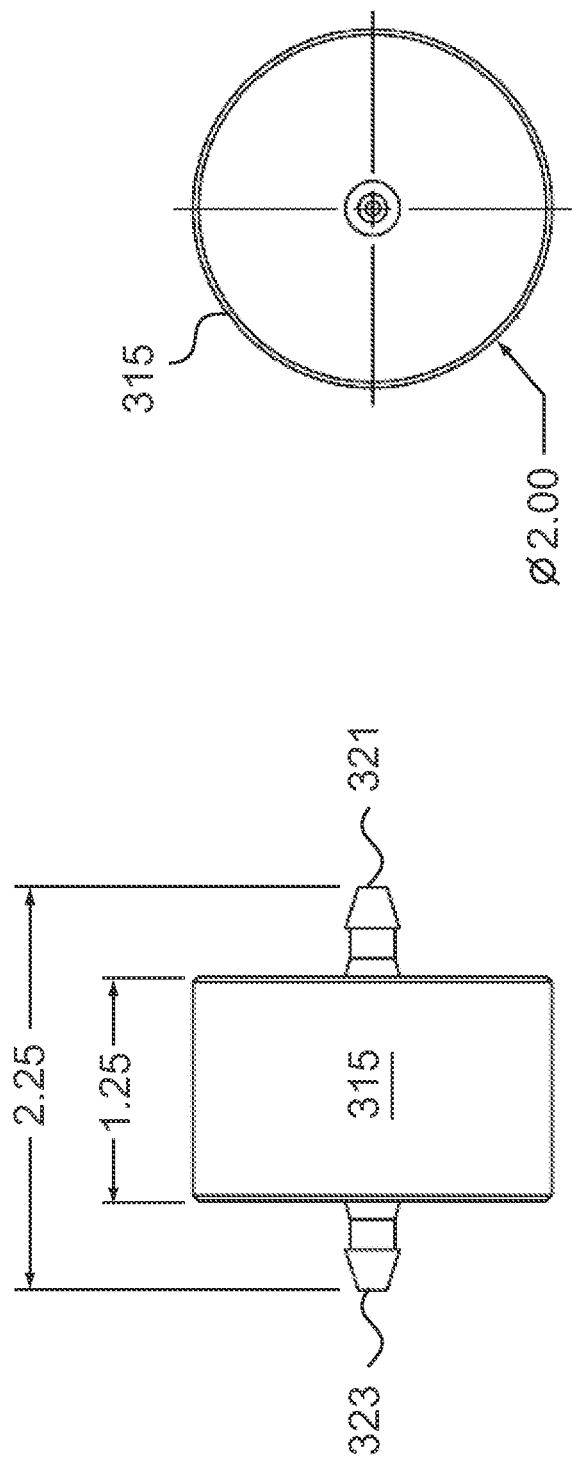

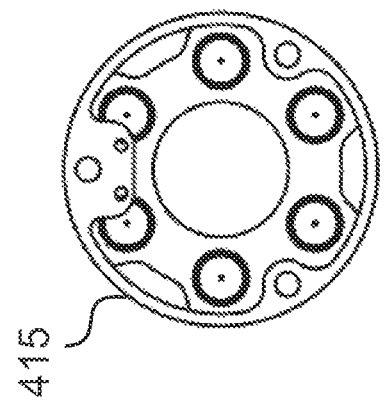
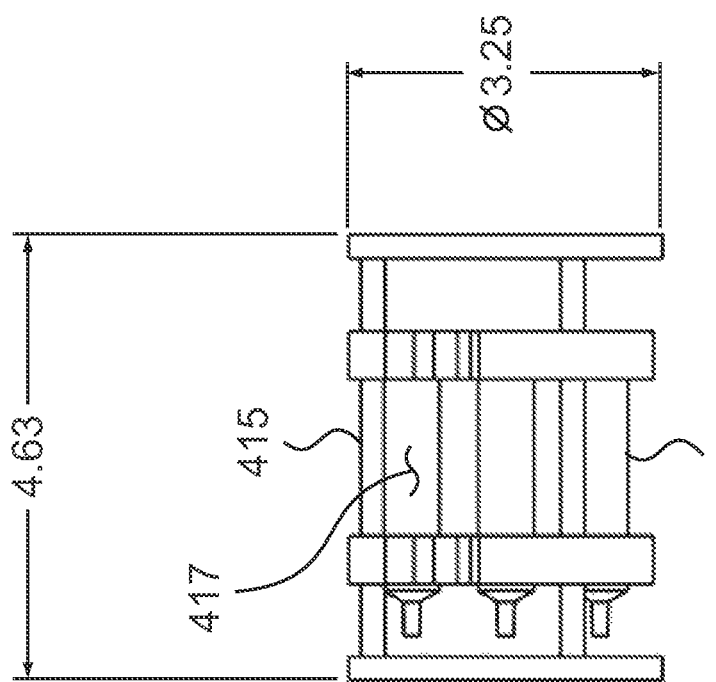

METHODS AND SYSTEMS FOR ULTRA-TRACE ANALYSIS OF LIQUIDS

CROSS-REFERENCE TO RELATED APPLICATIONS

This application claims the priority date of U.S. Provisional Application No. 61/331,482, filed May 5, 2010 and entitled "METHODS AND SYSTEMS FOR ULTRA-TRACE ANALYSIS OF LIQUIDS," the entire disclosure of which is incorporated by reference.

This application is also related to PCT International Patent Application No. PCT/US2009/01076 to Halden, filed Feb. 20, 2009, entitled "METHODS AND SYSTEMS FOR GROUND AND SURFACE WATER SAMPLING AND ANALYSIS," and published on Aug. 27, 2009 as WO2009/105241, which is incorporated by reference. The present invention is also related to U.S. patent application Ser. No. 12/702,033, filed Feb. 8, 2010 to Halden and entitled "METHODS AND SYSTEMS FOR FLUID EXAMINATION AND REMEDIATION." U.S. Ser. No. 12/702,033 is also incorporated by reference.

TECHNICAL FIELD

The present invention relates to engineering methods and systems enabling the use of advanced monitoring equipment for high-quality and ultra-sensitive analysis of liquid environments including groundwater monitoring wells. More particularly, the invention is directed to a system designed to capture and concentrate in a time-integrated fashion, ultra-low concentrations of dissolved and particulate materials present in liquid media (e.g., drinking water, surface water, groundwater, sea water).

BACKGROUND

Understanding the occurrence and movement of toxic chemicals and biological materials including microorganisms through liquid (e.g., aqueous) environments is essential for effective risk assessment and the protection of human health and the environment. The disclosed technology represents a major advance in environmental monitoring by enabling the cost-effective and ultra-sensitive detection of environmental contaminants of chemical and biological nature in natural and engineered waters.

As published in WO2009/105241, Halden, the inventor here, previously disclosed methods and kits for collection of dry samples from fluids such as ground, surface and tap water. Devices include a casing including a water intake zone wherein the casing encloses, a fluid reservoir, a pump, a non-aqueous collection matrix cartridge, and a waste water conduit, wherein the water intake zone, the fluid reservoir, the pump, the non-aqueous collection matrix cartridge, and the waste water conduit are all operably linked in sequence. However, that device required a multicompartment reservoir for collection of groundwater between the water intake zone and a pump.

The present disclosure represents an improvement over existing technologies by reducing to practice the concentration of chemical and biological contaminants from large-volume aqueous samples on low-volume extraction media that are integrated into field-deployable sampling devices for long-term, parallel sampling. As a further advance, there is no requirement for a multicompartment reservoir since, in some useful embodiments, the samples are concentrated and extracted into environmental/extraction cartridges.

BRIEF SUMMARY OF THE DISCLOSURE

This summary is provided to introduce a selection of concepts in a simplified form that are further described below in the Detailed Description. This summary is not intended to identify key features of the claimed subject matter, nor is it intended to be used as an aid in determining the scope of the claimed subject matter.

In one aspect, disclosed are methods and systems enabling the monitoring of chemical and biological constituents at hitherto unattainably low method detection limits. The technology can be used for environmental monitoring, tracking the progress and success of hazardous waste remediation, and for risk and exposure assessment.

In another aspect, a monitoring assembly with an intake has at least one pump featuring at least one pump channel mounted in the monitoring assembly. A plurality of fluid lines are coupled to the at least one pump. At least one filter cartridge, where each filter cartridge is separately coupled by one of the plurality of fluid lines to one of the pump channels, where each filter cartridge contains material for extracting an analyte, and where the at least one pump operates to separately push fluid through the at least one filter cartridge. The at least one filter cartridge operates to separate fluid into constituent parts.

BRIEF DESCRIPTION OF THE DRAWINGS

While the novel features of the invention are set forth with particularity in the appended claims, the invention, both as to organization and content, will be better understood and appreciated, along with other objects and features thereof, from the following detailed description taken in conjunction with the drawings, in which:

FIG. 1A-FIG. 1D schematically show an example embodiment of a device for simultaneous, parallel or sequential depletion/concentration of organic and inorganic chemical constituents as well as microorganisms from a liquid medium, such as groundwater, drinking water, and the like.

FIG. 3A and FIG. 3B schematically show a detailed top view and a detailed side view of a disk-shaped filter cartridge.

FIG. 5A and FIG. 5B schematically show a detailed side view and a top view of an example of an environmental/extraction module including a standard solid phase extraction media.

Figures 2A, 2B, 2C:
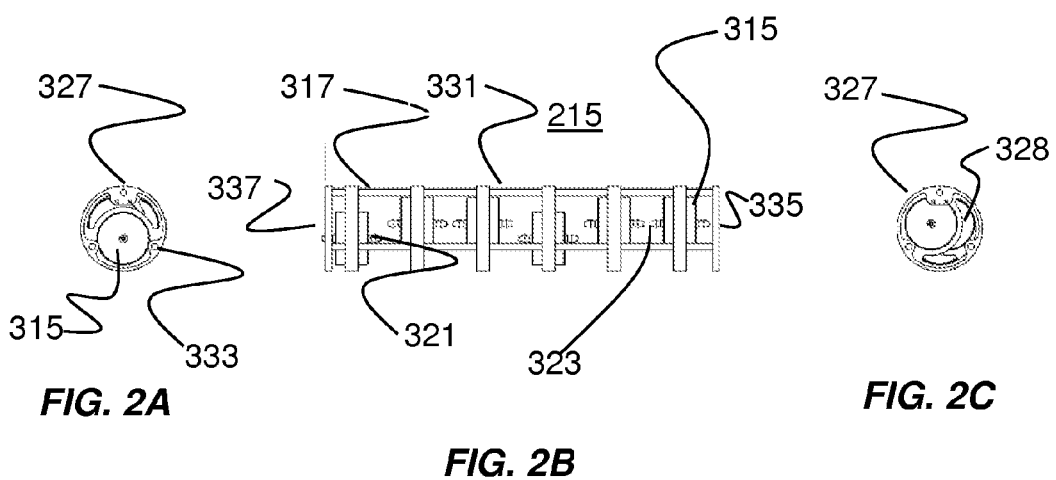
FIG. 2A-FIG. 2C schematically show one example configuration of detailed side, top and bottom views of a filter cartridge module allowing for the targeted depletion from water, and concentration on a (disk-shaped) filter cartridge, of organic and inorganic chemical constituents as well as microorganisms from liquid media.

In the drawings, identical reference numbers identify similar elements or components. The sizes and relative positions of elements in the drawings are not necessarily drawn to scale. For example, the shapes of various elements and angles are not drawn to scale, and some of these elements are arbitrarily enlarged and positioned to improve drawing legibility. Further, the particular shapes of the elements as drawn, are not intended to convey any information regarding the actual shape of the particular elements, and have been solely selected for ease of recognition in the drawings.

DETAILED DESCRIPTION OF THE PREFERRED EMBODIMENTS

The following disclosure describes several embodiments and systems for ultra-trace analysis of environmental waters. Several features of methods and systems in accordance with example embodiments are set forth and described in the Figures. It will be appreciated that methods and systems in accordance with other example embodiments can include additional procedures or features different than those shown in the Figures. Example embodiments are described herein with respect to wells. However, it will be understood that these examples are for the purpose of illustrating the principles, and that the invention is not so limited.

Additionally, methods and systems in accordance with several example embodiments may not include all of the features shown in these Figures. Throughout the Figures, identical reference numbers refer to similar or identical components or procedures.

Unless the context requires otherwise, throughout the specification and claims which follow, the word "comprise" and variations thereof, such as, "comprises" and "comprising" are to be construed in an open, inclusive sense that is as "including, but not limited to."

Reference throughout this specification to "one example" or "an example embodiment," "one embodiment," "an embodiment" or various combinations of these terms means that a particular feature, structure or characteristic described in connection with the embodiment is included in at least one embodiment of the present disclosure. Thus, the appearances of the phrases "in one embodiment," "in an embodiment," "in one example" or similar phrases in various places throughout this specification are not necessarily all referring to the same embodiment. Furthermore, the particular features, structures, or characteristics may be combined in any suitable manner in one or more embodiments.

Definitions

Generally, as used herein, the following terms have the following meanings when used within the context of methods for ultra-trace sampling of liquids:

"Analyte" is understood as any compound that may be present in a sample that can be captured using a non-aqueous collection matrix and detected using an assay or method.

By "cartridge" is meant a container enclosing the solid matrix through which the sample is passed through or over. The solid matrix is enclosed in the cartridge to allow the sample to pass through the cartridge, for example into an inlet port and out of an outlet port, wherein the solid matrix is retained within the cartridge.

By "concentration" or "concentration of the analyte" as used herein is understood as decreasing the volume in which a given mass of an analyte is present. For example, decrease the volume in which the given mass of the analyte is present by at least at least 2-fold, at least 10-fold, at least 102-fold, at least 103-fold, at least 104-fold, or at least 105-fold.

"Contacting" as used herein is understood as bringing two components into sufficient proximity (e.g., a groundwater sample containing or potentially containing an analyte and a non-aqueous collection matrix that can bind the analyte, a fluid sample and the water intake zone of the device) for sufficient time and under appropriate condition of temperature, pressure, pH, ionic strength, and the like to allow for the interaction of the two components, e.g., the binding of the analyte to the non-aqueous collection matrix, the entry of water into the device through the water intake zone. Contacting in the context of the invention typically occurs in a non-aqueous collection matrix container such as cartridge, column, or other device that allows the water to flow through the container in a path to allow the water to contact the non-aqueous collection matrix. Contacting a non-aqueous collection matrix cartridge is understood as contacting the matrix within the cartridge with the fluid sample.

"Control system" as used herein is understood as a device such as a computer or recording device. The control system can be used predominantly for mechanical uses, such as positioning the device in the well. The control system can also be used for turning on and off various components of the device, such as the pump, opening and closing fluid lines in the pump, directing collection of a time integrated or time discrete sample, and the like. The control system can also be used for the purpose of data collection in the form of electronic data, or by attachment to a chart recording device. The control system can be physically attached to the device by wires or cables. Alternatively, it can be integrated into the device. A wireless control system can be used with the device.

As used herein, "detecting", "detection" and the like are understood as an assay or method performed for identification of a specific analyte in a sample. The amount of analyte detected in the sample can be none (zero) or below the limit of detection (<LOD), positive and within the calibrated range, or positive and outside of the calibrated range of the assay or method.

"In situ" as used herein is understood as in the place where the assayed fluid flows (e.g., groundwater in the subsurface, preferably at or near the site that the sample is collected). "At or near the site that the sample is collected" is understood as at the same or similar depth such that pressure changes have little or no effect on the sample from the time that the sample is collected to the time that the sample is contacted with the non-aqueous matrix. It is understood that lateral movement within the well will typically have far less effect on pressure in the sample than movement in the depth in the well. In situ contacting of samples with a non-aqueous matrix is differentiated from contacting the non-aqueous matrix with the sample at the surface (i.e., ground level) when the sample is collected in the subsurface. It is understood that contacting surface water with the non-aqueous matrix at the site of collection (i.e., at ground level) is understood as contacting the sample with the matrix in situ.

As used herein, "non-aqueous analyte collection matrix", "matrix", "resin", and the like are understood as material or a mixture of materials that are designed to come into contact with the fluid sample and, through their relatively greater affinity relative to water, will remove and concentrate the analyte or analytes of interest from the fluid sample including dissolved solid, gas, and particulate materials of interest. For example, groundwater or surface water can be passed through, over, or mixed (i.e., contacted) with the non-aqueous analyte collection matrix, thereby causing this matrix to bind and concentrate one or more analytes. It is understood that the binding properties of the materials for one or more specific analytes can depend on various properties of the sampled fluid, for example, ionic strength, pH, and the like. The material can bind the analyte(s) specifically, e.g., chelator "Obtaining" is understood herein as manufacturing, purchasing, or otherwise coming into possession of.

"Operably linked" is understood as a connection, either physical or electronic, between two components of the device, or a component of the device and a remote sensor, data collector, controller, computer, or the like such that the components operate together as desired. For example, a fluid line operably linked to a non-aqueous collection matrix cartridge is understood as a fluid line that delivers fluid to the non-aqueous collection matrix cartridge without loss of fluid and at the desired flow rate. A device operably linked to the controller can be moved to the desired position in the well, and the pump or other components of the device can be turned on or off using the controller.

As used herein, "plurality" is understood to mean more than one. For example, a plurality refers to at least two, three, four, five, ten, 25, 50, 75, 100, or more.

As used herein, "real time" is understood as while the process is occurring, for example, collecting data, and preferably transmitting data to a device or person, at the same time the sample is being collected. The data need not be transmitted instantaneously, but is preferably transmitted within about 1 minute, 2 minutes, 5 minutes, 10 minutes, 15 minutes, or 30 minutes from the time that it was collected, or the collection of the data packet was completed. Data can be sent continuously or periodically in real time for monitoring the progress of a process, or can be sent episodically, e.g., upon overload of a non-aqueous collection matrix cartridge, failure of the device, detection of water table, completion of in well purge, and the like A "sample" or "fluid sample" as used herein refers to a material, particularly ground water, bulk water, pore water or surface water that is suspected of containing, or known to contain, an analyte. A fluid sample can include dissolved gases, as well as any dissolved or particulate solids. Methods and devices of the invention can be used for the collection of gases as well as dissolved or particulate solids upon selection of the appropriate non-aqueous collection matrix. A reference sample can be a "normal" sample, from a site known to not contain the analyte. A reference sample can also be taken at a "zero time point" prior to contacting the cell with the agent to be tested. A reference sample can also be taken during or after collection of a time integrated sample. A reference sample is typically a time discrete sample when it is collected at the same site as a time integrated sample.

Referring now jointly to FIG. 1 A-FIG. 1D, an example embodiment of a device for simultaneous, parallel or sequential depletion/concentration of chemical constituents from a liquid medium, such as groundwater, drinking water, and the like is shown. A modular monitoring assembly 201 includes an intake module 213, at least one pump module 210, and at least one filter cartridge module 215. For clarity's sake, not shown in this drawing are various cables, tubes and connectors that must be assembled prior to installation of the monitoring assembly into a well. However, it will be understood that fluidic and electrical connections are made conventionally. Bayonet closure mechanisms, similar to those used on SLR cameras, may be effectively employed on the module ends for making quick, reliable connections between different modules. ACME threads 219 (as shown in FIG. 1D) or similar tread types can also be used to assemble components and modules. See U.S. Ser. No. 12/702,033 as referenced above for more details.

FIG. 1B-FIG. 1D illustrate more details of the various modules. Note that in one useful embodiment, the modular design allows the various modules to be located within the monitoring assembly 201 in any desired arrangement or combination of arrangements. Due to the modular design, it is possible to scale the system up or down depending on the size of the well. For example, by changing the diameter of the snap-in column holders holding in place the plurality of test beds, larger test beds can be accommodated and housed in a tubular external housing of larger diameter. Each pump module may include a set of pump cartridges, a motor, and a set of rollers where the motor is connected to move the set of rollers in cooperation with the pump cartridges to peristaltically pump fluid.

In one example embodiment the plurality of intake ports may be advantageously fitted with a filter of a pore size suitable for allowing desirable chemical or biological constituents into the device but screening out larger particles, e.g., sand, that may lead to internal clogging of tubing and the test beds. The system of claim 1 further comprising a control system connected to control the plurality of pumps. Further, a power system is coupled to the control system. The power system may advantageously be a system selected from the group consisting of battery power, solar power, fuel cell power, generator power, transmission line supplied power and combinations thereof.

Figure 2D:
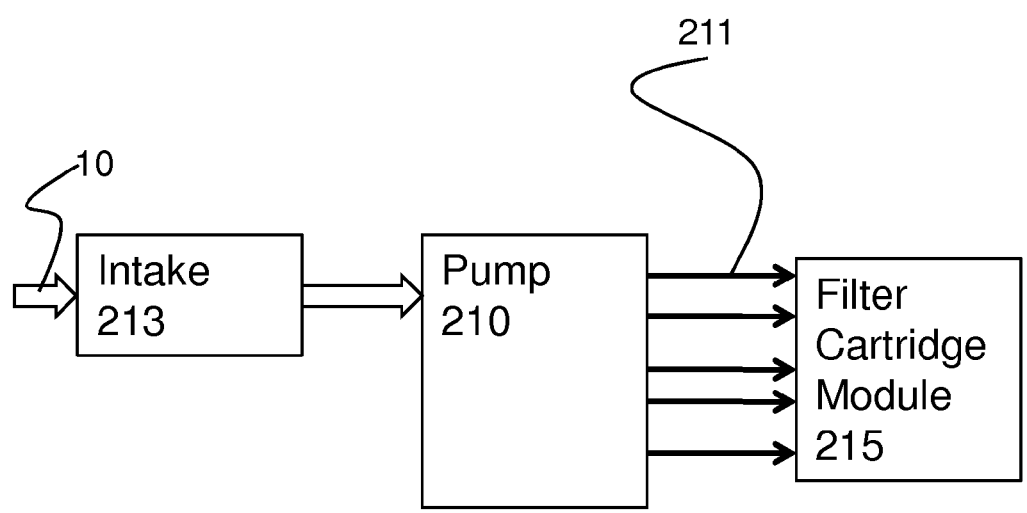
FIG. 2D schematically shows an example of fluid connections in a device as described in FIG. 1A-FIG. 1D.

Referrring now to FIG. 2A-FIG. 2C, detailed side, top and bottom views of a filter cartridge module allowing for the targeted depletion from water, and concentration on filter cartridges, of organic and inorganic chemical constituents as well as microorganisms from liquid media is shown. A filter cartridge module 215 includes a plurality of filter cartrige disks 315 that are arranged about the center axis 1 on a frame 317 to allow inlet ports 321 and outlet ports 323 to be connected to receive fluid flow from pump tubes (as shown in FIG. 2D) and output fluid through outlet tubes. Each of the plurality of filter cartrige disks 315 may be mounted in an offset mount 327 having apertures 328 that allow passage of the inlet and outlet tubes. The frame 317 includes connecting rods 331 that are of sufficient length to connect through alignment holes 333 in each of the offset mounts and fastened to a top mount 335 and a bottom mount 337. The offset mounts allow fluid tube connection access to the inlets and outlets.

Referring briefly to FIG. 2D an example of fluid connections in a device as described in FIG. 1A is schematically shown. Liquid 10 enters the intake 213 and flows through the pump module 210. The pump module 210 has a number of separate pump channels 211 that separately push fluid through separate filter cartridges in the at least one filter cartridge module.

Referrring now to FIG. 3A and FIG. 3B a detailed side view and a top view of a filter cartridge are shown. The filter cartridge 315 allows for the targeted concentration from a liquid of organic and inorganic chemical constituents as well as microorganisms. Each filter cartridge may contain a selected extraction cartridge material. The extraction cartridge materials are selected according to the analyte being analyzed using well-known principles.

Extraction cartridge materials for chemicals may advantageously include ion-exchange resins, activated carbon, molecular imprinted polymers, and the like. Filtration materials for biological sampling include cellulose acetate, nylon, polytetrafluoroethene (PTFE), metal screens, polyamide membranes, and molecular weight cutoff filters, and the like.

Suitable chemical analytes include but are not limited to:
Metals (alkali metals, alkaline earth metals, lanthanides, actinides, transition metals, and other metals and metalloids in the dissolved and particulate state and in various oxidation states), for example, cesium, magnesium, silver, arsenic, copper, iron, and the like,
Radionuclides in the dissolved and particulate state and in various oxidation states, for example, uranium, plutonium, and the like,
Non-metals (halogens, noble gases, other non-metals) in the dissolved and particulate state and in various oxidation states, for example, Cl, P, I, argon,
Inorganic compounds (nitrate, perchlorate, and the like), and
Organic compounds (chloroethenes, PCBs, dioxins, phthalates, pesticides, nitrosodimethyl amine (NDMA), and the like).

Suitable biological analytes of natural and artificial origin (e.g., genetically engineered), include but are not limited to:
Viruses (e.g., Norovirus, HIV, hepatitis viruses, MS2 bacteriophage, enteric viruses, and the like, as well as non-naturally occurring, engineered infectious particles),
Bacteria (e.g., *E. coli, Salmonella, Streptococci, Legionella*, as well as spore-forming organisms such as *Bacilli* and *Clostridia* and their respective spores),
Fungi and molds (*Aspergillus niger*, and fungal spores from this and other species),
Parasites (e.g., *Cryptosporidium* spp., *Microsporidium* spp., oocysts of parasites, *Giardia lamblia*, and the like, and
Prions ($PrP^{Sc}$ and others).

For more information on chemical and microbial contaminants, refer to the EPA website at http://www.epa.gov/safewater/contaminants/index.html.

Figures 4A, 4B:
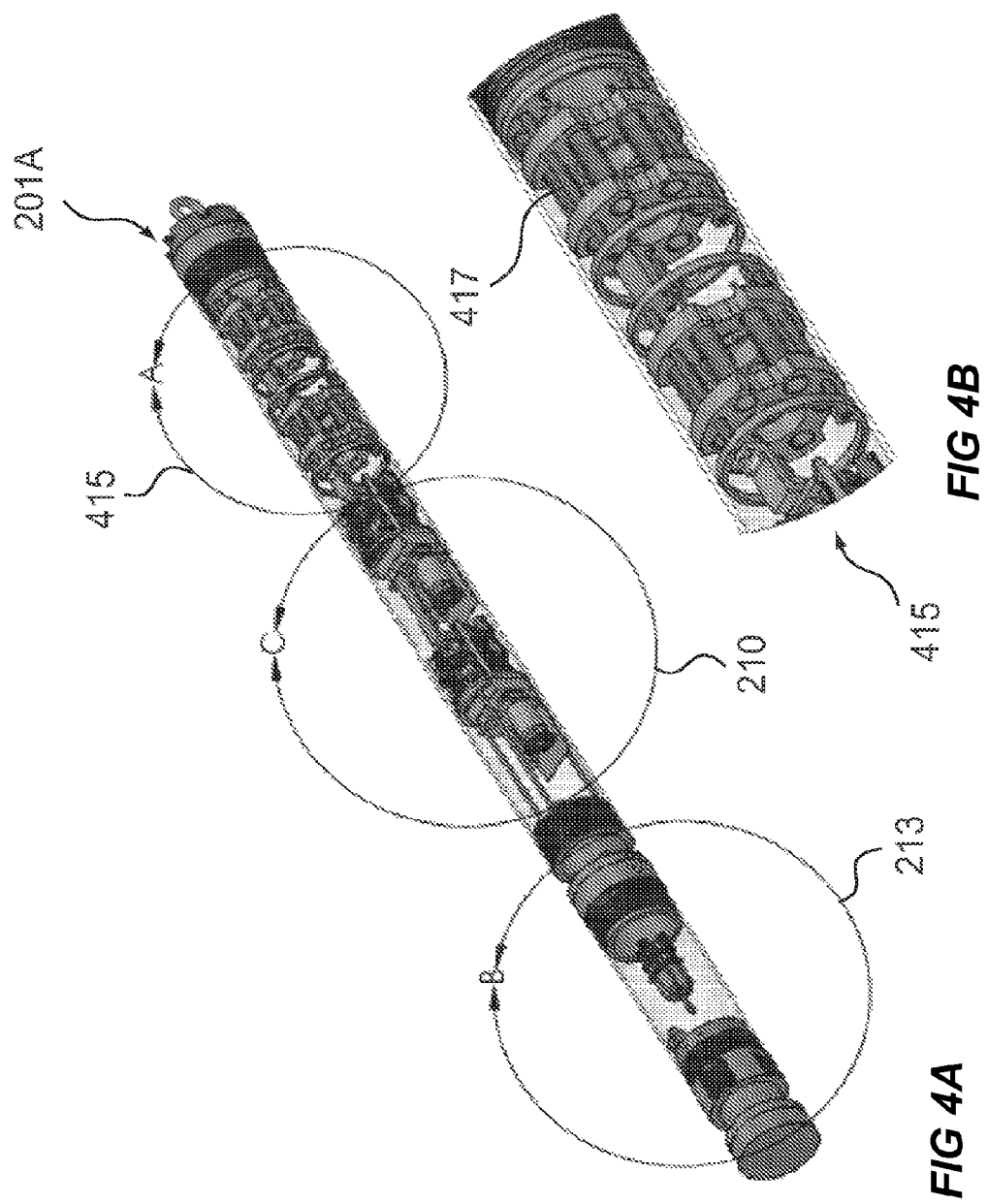
FIG. 4A schematically shows an alternate embodiment of a mounting arrangement for a device as described with respect to FIG. 1A.
FIG. 4B is a more detailed view of an environmental/extraction module.

Referring now to FIG. 4A an alternate embodiment example of a mounting arrangement for a device as described with respect to FIG. 1A is schematically shown. A modular monitoring assembly 201A includes an intake module 213, at least one pump module 210, and at least one environmental/extraction module 415. For clarity's sake, not shown in this drawing are various cables, tubes and connectors that must be assembled prior to installation of the monitoring assembly into a well. However, it will be understood that fluidic and electrical connections are made conventionally. The alternative modular system is otherwise constructed substantially similarly to assembly 201 as described hereinabove.

FIG. 4B illustrates more details of an environmental/extraction module 415. In one embodiment the environmental/extraction module 415 advantageously includes a cartridge containing a solid phase extraction media 417.

Referring now to FIG. 5A and FIG. 5B a detailed side view and a top view of an example of environmental/extraction module containing standard solid phase extraction media are shown. In one embodiment, the environmental/extraction module 415 includes a plurality of extraction cartridges 418 containing solid phase extraction media 417. The plurality of extraction cartridges 418 are arranged in parallel to allow for parallel, targeted concentration of organic and inorganic chemical constituents and microorganisms from liquid media. Standard solid phase extraction media may comprise glass cartridges that are filled with a selected extraction material. Such cartridges are commercially available from vendors such as Applied Separations, Inc. of Allentown, Pa., US. Glass cartridges are available prefilled with a packing/sorbent of choice, depending on the analyte. The use of glass is advantageous as it limits sorption of hydrophobic compounds to the filter housing. Clear glass has the further advantage of allowing visual inspection of accumulated materials.

Figure 6:
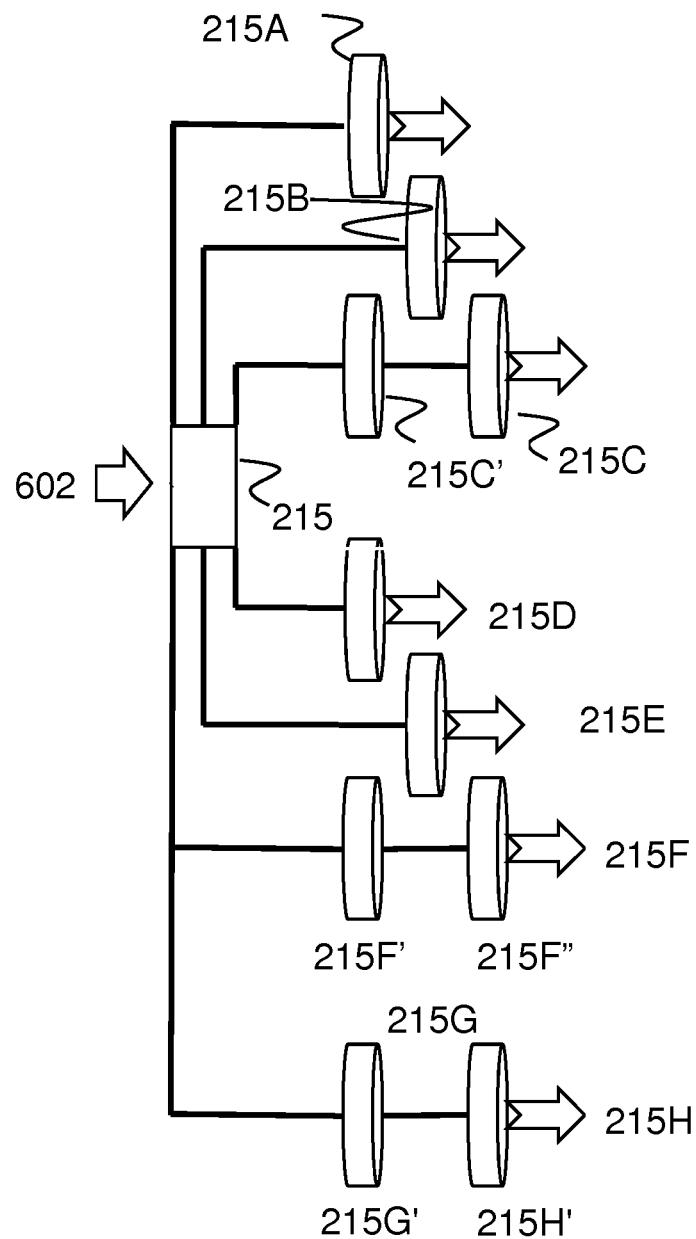
FIG. 6 schematically shows the use of a filter cartridge module to fractionate water constituents.

Referring now to FIG. 6, the use of a filter cartridge module to fractionate water constituents is shown. Fluid flow into a filter cartridge module 215 is indicated by arrow 602. The filter cartridge module 215 fractionates the water into a plurality of constituents corresponding to different filter cartridges that are schematically illustrated as constituents 215A-215H. For example, constituent 215A may advantageously use a 3-µm filter disk to concentrate oocysts of Cryptosporidium on the filter and produces Cryotosporium-depleted effluent. Constituent 215B may advantageously use a 0.2-µm filter disk to concentrate biomass except for viruses on the filter and produces biomass-depleted effluent. Constituent 215C may advantageously use a 3-µm filter disk 215C' and a 0.2-µm filter disk in sequence to reduce the risk of clogging of the 0.2 µm-filter. Constituent 215D may advantageously use an anion exchange disk to concentrate target anions on the disk and produces anion-conditioned effluent. Constituent 215E may advantageously use a disk cartridge filled with molecularly imprinted polymer (MIP) or solid phase extraction (SPE) resin to concentrate desired organic compounds on the disk and produces effluent depleted in these specific compounds. Constituent 215F may advantageously use an anion exchange 215F' and MIP/SPE disk 215F" in sequence to concentrate select anions and organic compounds on the disks and produces effluent depleted in select anions and organic compounds. Constituents 215G and 215H may advantageously use two (215G' and 215H') or more identical disk cartridges arranged in series for complete removal of an analyte of interest. Complete depletion of the analyte from constituent 215G can be proven experimentally by analysis of cartridge 215H'. Showing absence of said analyte in cartridge 215H' enables closure of the mass balance for the analyte of interest via extraction and analysis of the analyte mass captured in cartridge 215G'.

Figure 7:
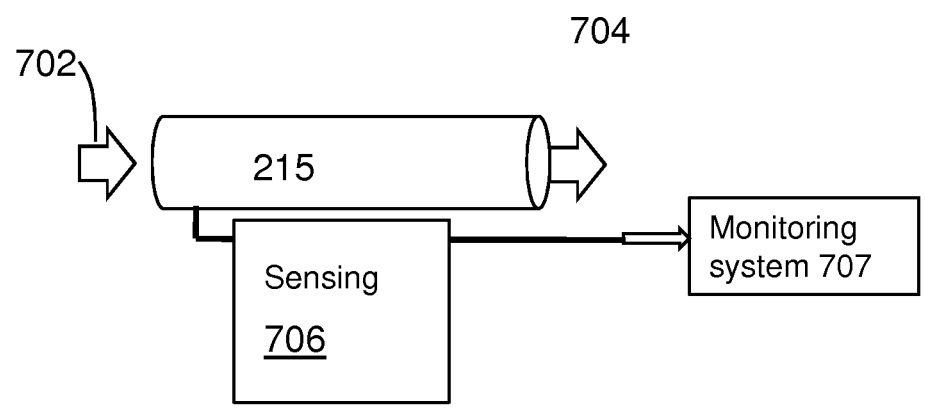
FIG. 7 schematically shows an example of the utility of a filter cartridge module for monitoring of a water supply.

Referring now to FIG. 7, an example of the utility of a filter cartridge module for monitoring of a water supply is shown. Fluid flow into the inlet port of the filter cartridge module 215 is indicated by directional arrow 702 and outlet flow is indicated by arrow 704. A conventional in-line sensing device 706 allows for simultaneous capture and concentration of microorganisms and chemical constituents on separate filters and extraction media. Cartridge module 215 may be analyzed post sampling in off-line mode for both microbial and chemical constituents. Alternatively, data also can be sent via wireless transmission, cable or wire to a monitoring system 707. The at least one sensing unit may include sensors selected from the group consisting of real-time sensors, monitoring equipment, acidity (pH), oxidation/reduction potential (Eh), dissolved oxygen (DO), ion-specific electrodes and chemical sensors, a temperature sensor, an ion-specific electrode, a biochemical sensor, an electrochemical sensor, a tuning fork sensor, and combinations thereof. Monitoring system 707 may comprise a personal computer or similar equipment suitable for storing, analyzing and/or displaying data.

Figure 8:
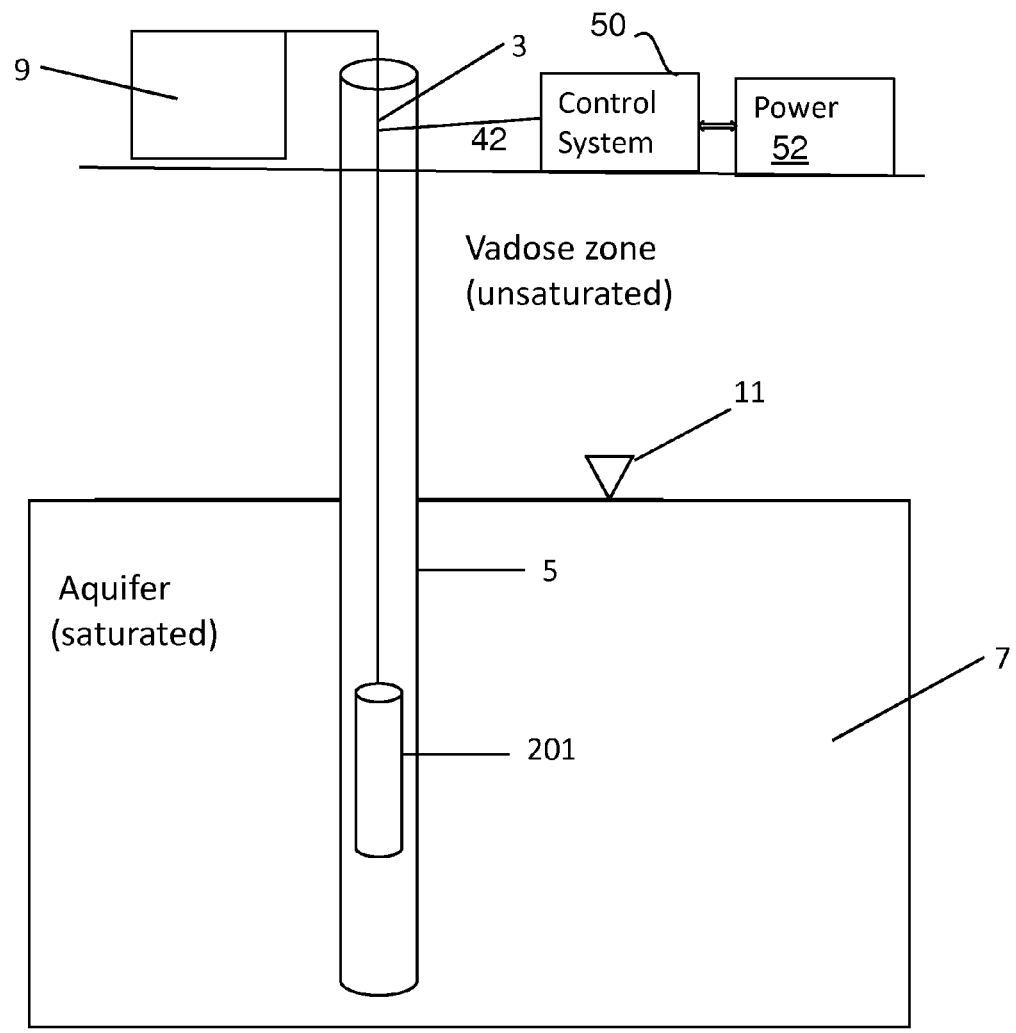
FIG. 8 schematically shows an example of the utility of filter cartridge modules for use in a groundwater monitoring well.

Referring now to FIG. 8, an example of the utility of a filter cartridge module in a groundwater monitoring well is shown. A well 5, contains an in situ well sampling system assembled substantially as described above with reference to FIG. 1A or FIG. 4A, for example. The assembly is tethered by a cable bundle 3 to a stable platform 9. In one example application the assembly may be positioned below the unsaturated Vadose zone and below the groundwater table 11 in the aquifer 7. In this configuration, the in situ well system can serve to sample and process groundwater.

Figure 9:
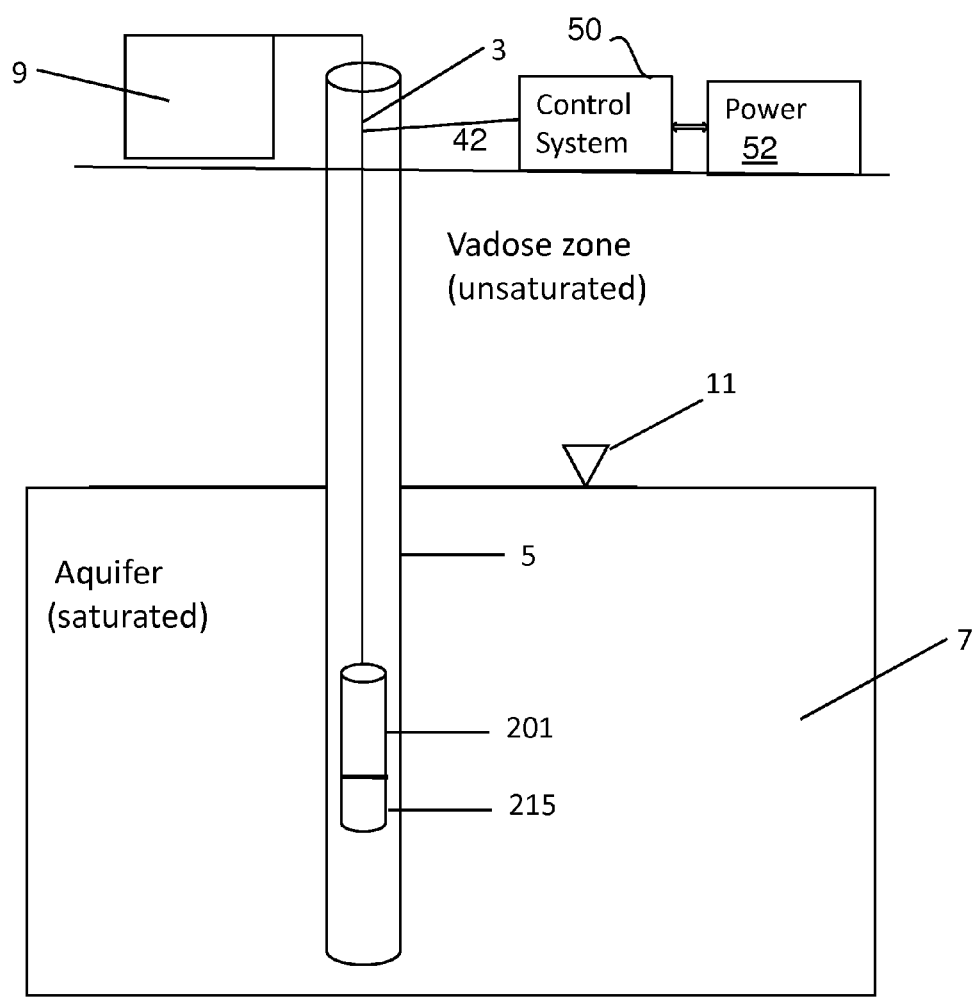
FIG. 9 schematically shows an example of the utility of filter cartridge modules for use with in situ microcosm array technology.

Referring now to FIG. 9, an example of the utility of a filter cartridge module in a groundwater monitoring well for use with in situ microcosm array technology (201) is shown. Water exiting select sediment microcosms passes through a filter cartridge module 215 located downstream of the sediment microcosms and upstream of the effluent collection vessels, if used. This configuration enables removal of select microorganisms and select chemicals from sediment column effluent.

Figure 10:
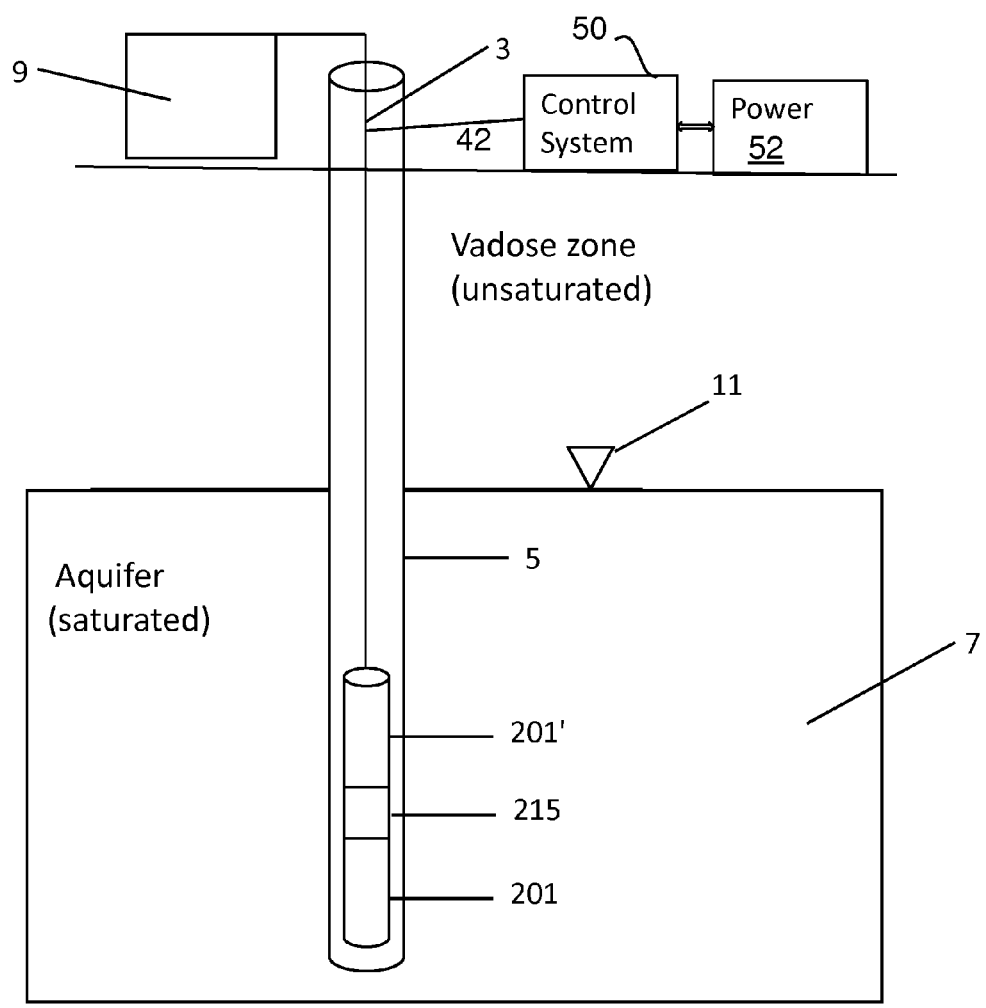
FIG. 10 schematically shows an example of the utility of two filter cartridge modules for conditioning of groundwater prior to entry into in situ and ex situ microcosms with post-processing of microcosm effluent in the second filter cartridge module.

Referring now to FIG. 10, an alternative use of two filter cartridge modules in conjunction with the in situ microcosm array technology (201) is shown. Water taken from the well is first pre-processed in filter cartridge module 201 and then allowed to enter the in situ microcosm array technology (201), whose effluent is processed via passage through a second filter cartridge module 201'. This arrangement enable removal of select chemicals and microorganisms from the groundwater prior to testing in the in situ microcosm array technology, as well as post-processing of the effluent of the microcosm array for capture and determination of chemicals and microorganisms in microcosm effluent.

In FIGS. 8, 9 and 10, the at least one pump may advantageously be controlled by a control system 50 located in one embodiment on the ground surface and in communication with the sampling system as generally indicated by control line 42 and powered by a power system 52. The power system 52 may include any power setup useful for remote locations such as battery power, solar power, fuel cell power, generator power, transmission line supplied power or the like. Using independent power generation from solar panels, storage batteries and equivalent devices, the unit may be operated off the grid with DC current provided for continuous "around-the-clock" operation, day and night.

Figure 11:
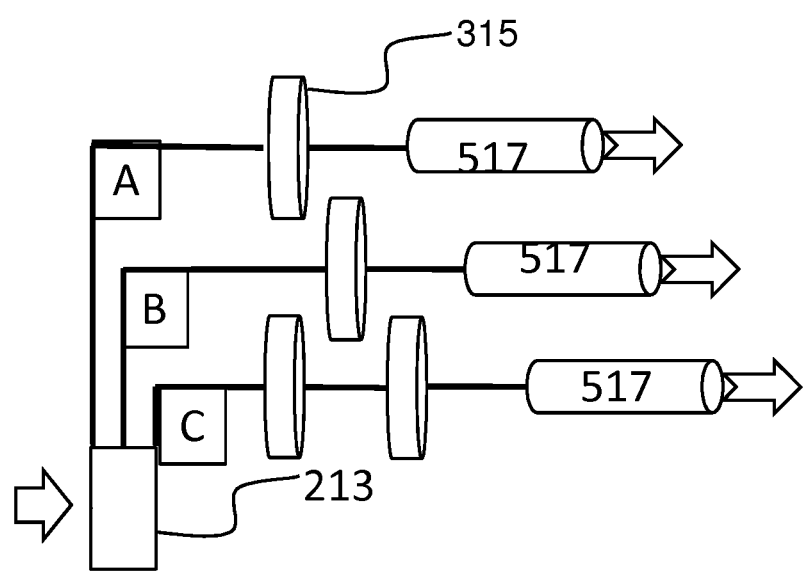
FIG. 11 schematically shows an example of the utility of filter cartridge modules for conditioning of groundwater prior to entry into in situ and ex situ microcosms.

Referring now to FIG. 11, an example of the utility of a filter cartridge module for conditioning of groundwater prior to entry into in situ and ex situ microcosms is schematically shown. In the example, environmental/extraction cartridges comprise test beds 517. A test bed provides an environment for materials to interact. Such materials could be chemicals, microbes, and the like or a combination thereof. A test bed may be a microcosm, a biotrap, a reactor, or similar devices. Groundwater entering the microcosms can be pre-conditioned by removing select microorganisms (A), select chemicals (B), or both (C).

In one useful application the system disclosed herein includes biotrap filters. Use of the system with biotrap filters allows the biotraps to benefit from the concept of controlled flow and pre-conditioning and post-conditioning of fluids, such as, for example, groundwater. Biotrap systems are commercially available from Microbial Insights, Inc. of Rockford, Tenn., US. The utility of this disclosure eliminates important drawbacks of biotraps as previously used. For example, as used conventionally without the benefit of the teachings of this disclosure, the flow of water past the biotrap is not preconditioned and the volume of water in contact with the biotrap over time is unknown. Thus quantitative analysis of the flow is problematic, unreliable or impossible. Further, loss of isotopically labeled substances used in the biotrap could be monitored using the concepts shown here which would enable a complete mass balance on isotopes. Pre-conditioning of water prior to entry of the microcosm (sediment microcosm or biotrap) could help to deduce what reactions are microbially mediated and what reactions are abiotic.

Figure 12:
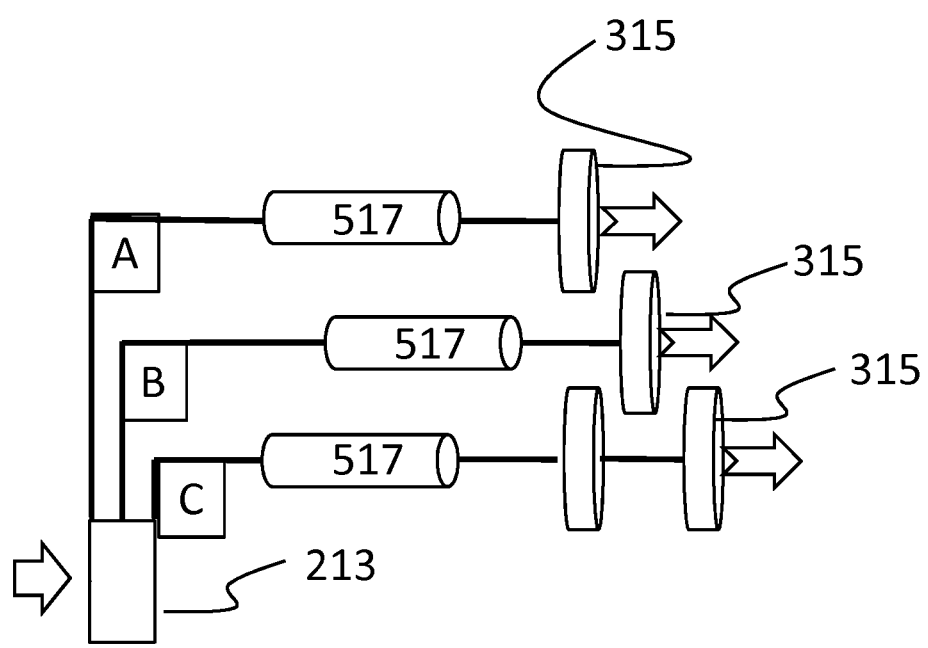
FIG. 12 schematically shows an alternate example of the utility of filter cartridge modules for processing of water exiting in situ and ex situ microcosms.

Referring now to FIG. 12, an alternate example of the utility of filter cartridge modules for processing of water exiting in situ and ex situ microcosms is schematically shown. Water is pumped at a predetermined flow rate through, for example, test beds 517 comprising microcosms, and is then forced through appropriate in-line filter cartridges 315 to remove select microorganisms (A), select chemicals (B), or both (C).

Figure 13:
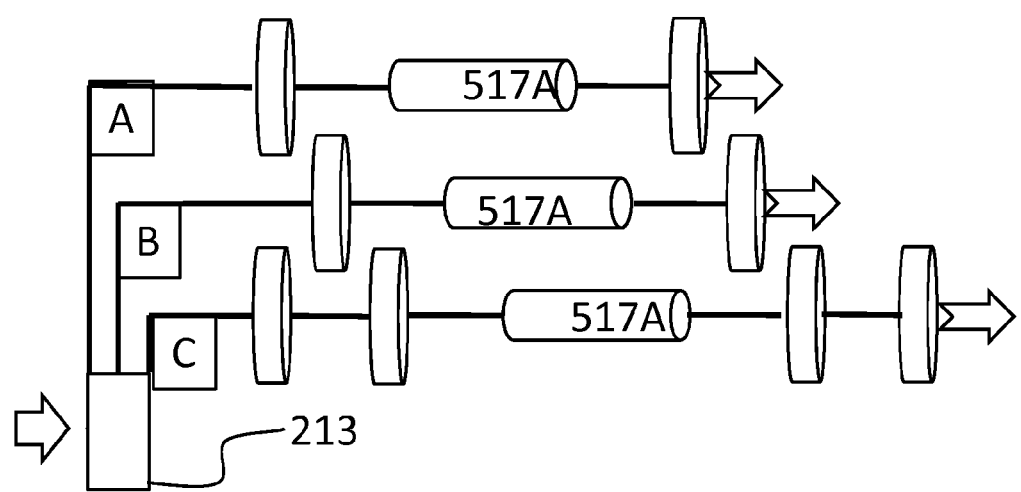
FIG. 13 schematically shows another alternate example of the utility of filter cartridge modules for conditioning a liquid medium entering into in situ or ex situ microcosms and subsequent processesing of the microcosm effluent.

Referring now to FIG. 13 another alternate example of the utility of filter cartridge modules for conditioning a liquid medium entering into in situ or ex situ microcosms 517A and subsequent processesing of the microcosm effluent, again using the disk array approach is schematically shown. Water is pumped at a predetermined flow rate through one (A, B) or more filter cartridges (C) and this pre-conditioned water, after passage through each microcosm 517A, then passes through one (A, B) or more (C) additional in-line disks to collect select microorganisms, select chemicals, or both.

Figures 14A, 14B:
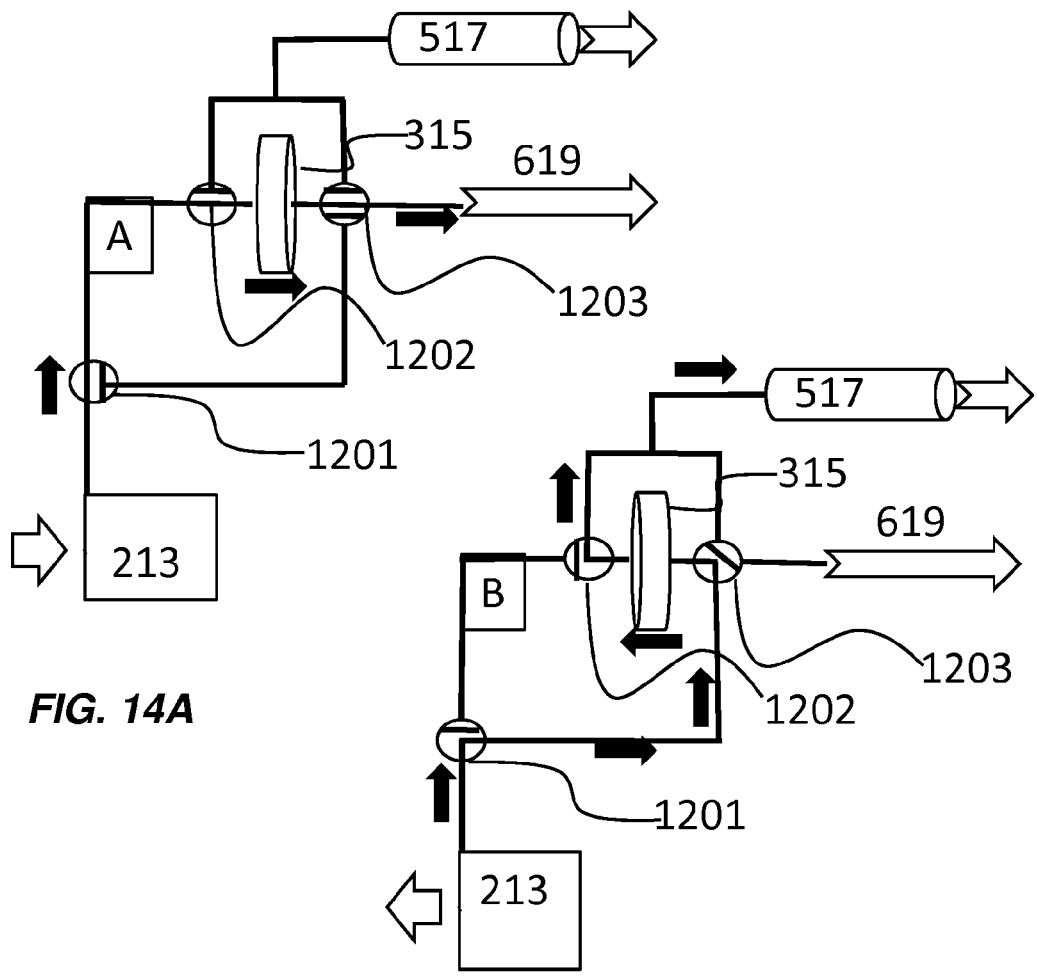
FIG. 14A and FIG. 14B schematically shows an example of the utility of filter cartridge modules to preconcentrate microorganisms for use with in situ microcosm arrays.

Referring now jointly to FIG. 14A and FIG. 14B, an example of the utility filter cartridge modules to preconcentrate microorganisms for use in in situ microcosm arrays is schematically shown. In FIG. 14A, showing step A, microbes suspended in water are captured on a solid medium or on a filtration disk 315. Unwanted filtrate can be discharged as effluent 619. In FIG. 14B, showing step B, the flow direction of water is reversed by use of one or more valves (1201, 1202, 1203) and the concentrated microbes are flushed from the filter disk 315 into a test bed 517 comprising, for example, a microcosm, for studying their survival and interaction with chemicals of interest. Use of 3 valves, 1201, 1202, 1203 can allow for loading of the filter (Step 1) and eluting concentrated microorganisms from the filter (Step 2) in a 2-step process.

The invention has been described herein in considerable detail in order to comply with the Patent Statutes and to provide those skilled in the art with the information needed to apply the novel principles of the present invention, and to construct and use such exemplary and specialized components as are required. However, it is to be understood that the invention may be carried out by specifically different equipment, and devices, and that various modifications, both as to the equipment details and operating procedures, may be accomplished without departing from the true spirit and scope of the present invention.

What is claimed is:

1. A method for monitoring comprising:
   locating an assembly in a well including at least one pump and at least one filter cartridge module wherein each filter cartridge module includes a plurality of filter cartridges;
   connecting the at least one filter cartridge module through a plurality of pump channels to the at least one pump;
   operating the at least one pump to push water through each of the plurality of filter cartridges at a predetermined flow rate, where each of the plurality of filter cartridges holds material for extracting an analyte; and wherein the plurality of filter cartridges operates to separate fluid into constituent parts;

pumping water at a predetermined flow rate through the at least one filter cartridge module to produce pre-conditioned water;

passing the preconditioned water through at least one microcosm, then passing water flowing through the at least one microcosm through at least one additional in-line filter cartridge to collect select microorganisms, select chemicals, or both.

2. The method of claim 1 further comprising incorporating at least one environmental/extraction module to receive fluid flowing through the at least one filter cartridge module.

3. The method of claim 1 where the extraction material is selected for extracting chemicals from the group consisting of ion-exchange resins, hydrophilic-hydrophobic interaction polymers, activated carbon, molecular imprinted polymers, polymers featuring analyte-specific docking sites, and combinations thereof.

4. The method of claim 1 where the extraction material is selected from the group consisting of cellulose inorganic polymers, organic polymers, acetate, nylon, polytetrafluoroethene (PTFE), metal screens, polyamide membranes, and molecular weight cutoff filters, and combinations thereof.

5. The method of claim 1 wherein the extraction material is selected for extracting chemical analytes selected from the group consisting of metals, alkali metals, alkaline earth metals, lanthanides, actinides, transition metals, metals and metalloids in the dissolved and particulate state and in various oxidation states, cesium, magnesium, silver, arsenic, copper, iron, and alloys thereof, radionuclides in the dissolved and particulate state and in various oxidation states, uranium, plutonium, halogens, noble gases, in the dissolved and particulate state and in various oxidation states including Cl—, P, I, argon, inorganic compounds, nitrate, perchlorate, and combinations thereof and organic compounds, chloroethenes, PCBs, dioxins, phthalates, pesticides, nitrosodimethyl amine, NDMA, and combinations thereof.

6. The method of claim 1 wherein the extraction material is selected for extracting biological analytes of natural and artificial origin selected from the group consisting of proteins, lipids, DNA, RNA, viruses, norovirus, HIV, hepatitis viruses, MS2 bacteriophage, enteric viruses, non-naturally occurring engineered infectious particles, bacteria, *E. coli, Salmonella, Streptococci, Legionella*, spore-forming organisms, *Bacilli, Clostridia* and their respective spores, Fungi and molds, *Aspergillus niger*, fungal spores, parasites, *Cryptosporidium* spp., *Microsporidium* spp., oocysts of parasites, *Giardia lamblia*, prions including $PrP^{Sc}$.

7. The method of claim 1 further comprising connecting at least one sensing unit to receive fluid from the plurality of filter cartridges.

8. The method of claim 1 further comprising connecting at least one sensing unit to receive fluid from at least one of the plurality of filter cartridge modules, where the at least one sensing unit includes sensors selected from the group consisting of real-time sensors, monitoring equipment, acidity (pH), oxidation/reduction potential (Eh), dissolved oxygen (DO), ion-specific electrodes and chemical sensors, a temperature sensor, an ion-specific electrode, a biochemical sensor, an electrochemical sensor, a tuning fork sensor, and combinations thereof.

9. The method of claim 7 wherein the at least one sensing unit transmits data to a monitoring system.

10. The method of claim 1 wherein the at least one pump comprises at least one peristaltic pump.

11. The method of claim 2 wherein the at least one environmental/extraction module comprises a test bed module including at least one test bed.

12. The method of claim 1 further comprising:
capturing suspended microbes on a solid medium or on a filtration disk; and
reversing the flow direction of the water to flush the concentrated microbes into a microcosm.

13. The method of claim 1 further comprising operating a first valve for backwashing of the filter cartridge; and operating a second valve to bypass the filter cartridge.

* * * * *